(12) United States Patent
Wilkinson (10) Patent No.: US 12,025,486 B2
(45) Date of Patent: Jul. 2, 2024

(54) MEMS SENSING SYSTEM

(71) Applicant: Tactual Labs Co., New York, NY (US)

(72) Inventor: David Clark Wilkinson, Austin, TX (US)

(73) Assignee: Tactual Labs Co., New York, NY (US)

( * ) Notice: Subject to any disclaimer, the term of this patent is extended or adjusted under 35 U.S.C. 154(b) by 233 days.

(21) Appl. No.: 16/909,608

(22) Filed: Jun. 23, 2020

(65) Prior Publication Data

US 2020/0408592 A1  Dec. 31, 2020

Related U.S. Application Data (60) Provisional application No. 62/866,206, filed on Jun. 25, 2019.

(51) Int. Cl.
| | |
|---|---|
| *G01H 11/06* | (2006.01) |
| *G01P 13/00* | (2006.01) |
| *H01Q 1/27* | (2006.01) |
| *H04R 19/04* | (2006.01) |

(52) U.S. Cl.
CPC ............ *G01H 11/06* (2013.01); *G01P 13/00* (2013.01); *H01Q 1/273* (2013.01); *H04R 19/04* (2013.01); *H04R 2201/003* (2013.01)

(58) Field of Classification Search
CPC ........ G01H 11/06; G01P 13/00; H01Q 1/273; H04R 19/04; H04R 2201/003; H04R 17/02; A61B 2562/0204; A61B 2562/028; A61B 5/1125; A61B 5/681; A61B 5/7257; A61B 5/1123; G01S 13/50; G01S 7/356; G01S 7/358; G01S 13/347; G06F 3/014; G06F 3/017; G06F 3/04142; G06F 3/0488; G06F 2200/1637; G06F 1/163; G06F 1/1694
See application file for complete search history.

(56) References Cited

U.S. PATENT DOCUMENTS

| | | | | |
|---|---|---|---|---|
| 6,964,640 | B2 * | 11/2005 | Zumeris | A61B 8/4483 600/459 |
| 11,347,312 | B1 * | 5/2022 | Wang | G06F 3/016 |
| 2015/0091790 | A1 * | 4/2015 | Forutanpour | G06F 3/011 345/156 |
| 2015/0215443 | A1 * | 7/2015 | Heo | H04M 1/05 455/556.1 |
| 2015/0370326 | A1 * | 12/2015 | Chapeskie | G06F 1/163 345/156 |
| 2016/0022223 | A1 * | 1/2016 | Grundfest | A61B 5/7278 600/407 |

(Continued)

*Primary Examiner* — Angelica M McKinney
(74) *Attorney, Agent, or Firm* — Adam B. Landa; Tod A. Kupstas (57) ABSTRACT

A sensing system implements one or more MEMS microphones in order to measure mechanical waves. The sensing system can be part of a larger system used to determine motion and position of a user's hand or other body part. The MEMS microphones can be part of a plurality of MEMS microphones. There may additionally be MEMS microphones that transmit mechanical waves at certain frequencies that can be measured by the MEMS microphones and subsequently distinguished from other mechanical waves and used to determine additional information regarding movement and position.

6 Claims, 5 Drawing Sheets

(56) References Cited

U.S. PATENT DOCUMENTS

| | | | |
|---|---|---|---|
| 2017/0086742 A1* | 3/2017 | Harrison-Noonan | A61B 5/6843 |
| 2018/0348877 A1* | 12/2018 | Chan | H04R 1/028 |
| 2019/0369731 A1* | 12/2019 | Verbeke | G06F 3/016 |
| 2020/0026352 A1* | 1/2020 | Wang | G06F 3/044 |
| 2020/0133398 A1* | 4/2020 | Williams | G06F 3/017 |

* cited by examiner

MEMS SENSING SYSTEM

This application claims the benefit of U.S. Provisional Application Ser. No. 62/866,206, filed Jun. 25, 2019, the contents of which are incorporated herein by reference. This application includes material which is subject to copyright protection. The copyright owner has no objection to the facsimile reproduction by anyone of the patent disclosure, as it appears in the Patent and Trademark Office files or records, but otherwise reserves all copyright rights whatsoever.

FIELD

The disclosed apparatus and method relate to the field of sensors, in particular the disclosed apparatus and method relate to gesture and human interaction sensors operating through the acoustic (mechanical wave) sensing of motion and position.

BRIEF DESCRIPTION OF THE DRAWINGS

The foregoing and other objects, features, and advantages of the disclosure will be apparent from the following more particular description of embodiments as illustrated in the accompanying drawings in which reference characters refer to the same parts throughout the various views. The drawings are not necessarily to scale, emphasis instead being placed upon illustrating principles of the disclosed embodiments.

DETAILED DESCRIPTION

The presently disclosed systems and methods involve principles related to and for designing, manufacturing and using sensors implementing acoustic signals (mechanical waves). The acoustic signals are used with devices that may be able to transmit and receive the signals by themselves or function in conjunction with other devices that implement and transmit other types of signals or use other types of sensing modalities. By acoustic signals it is meant signals that are generated via the transmission of waves through a medium, such as gas and solids. Generally acoustic signals may be referred to as mechanical waves.

Throughout this disclosure, the term "event" may be used to describe periods of time in which muscle activity and/or position of the body is detected and determined. In accordance with an embodiment, events may be detected, processed, and/or supplied to downstream computational processes with very low latency, e.g., on the order of ten milliseconds or less, or on the order of less than one millisecond.

As used herein, and especially within the claims, ordinal terms such as first and second are not intended, in and of themselves, to imply sequence, time or uniqueness, but rather, are used to distinguish one claimed construct from another. In some uses where the context dictates, these terms may imply that the first and second are unique. For example, where an event occurs at a first time, and another event occurs at a second time, there is no intended implication that the first time occurs before the second time, after the second time or simultaneously with the second time. However, where the further limitation that the second time is after the first time is presented in the claim, the context would require reading the first time and the second time to be unique times. Similarly, where the context so dictates or permits, ordinal terms are intended to be broadly construed so that the two identified claim constructs can be of the same characteristic or of different characteristics. Thus, for example, a first and a second frequency, absent further limitation, could be the same frequency, e.g., the first frequency being 10 Mhz and the second frequency being 10 Mhz; or could be different frequencies, e.g., the first frequency being 10 Mhz and the second frequency being 11 Mhz. Context may dictate otherwise, for example, where a first and a second frequency are further limited to being frequency-orthogonal to each other, in which case, they could not be the same frequency.

The system described herein uses acoustic signals in order to determine motion and position. In an embodiment, the system described herein senses the motion and position of a person's body part. In an embodiment, the system described herein senses the motion and position of a person's hand. In an embodiment, the system described herein senses the motion and position of a person's fingers. In an embodiment, the system described herein senses the motion and position of a person's legs. In an embodiment, the system described herein senses the motion and position of a person's arms. In an embodiment, the system described herein senses the motion and position of a person's head. In an embodiment, the system described herein senses the position of a person with respect to another person. In an embodiment, the system described herein senses the motion of a person with respect to a device or an object.

An embodiment of the disclosure implements MEMs (micro-electromechanical system) microphones. MEMs microphones are transducers that convert acoustic (mechanical) pressure waves to electrical signals. The MEMs microphones can be arranged in an array or placed in various locations depending on the desired implementation. Additionally one MEMs microphone can be used instead of multiple MEMs microphones.

Figure 1:
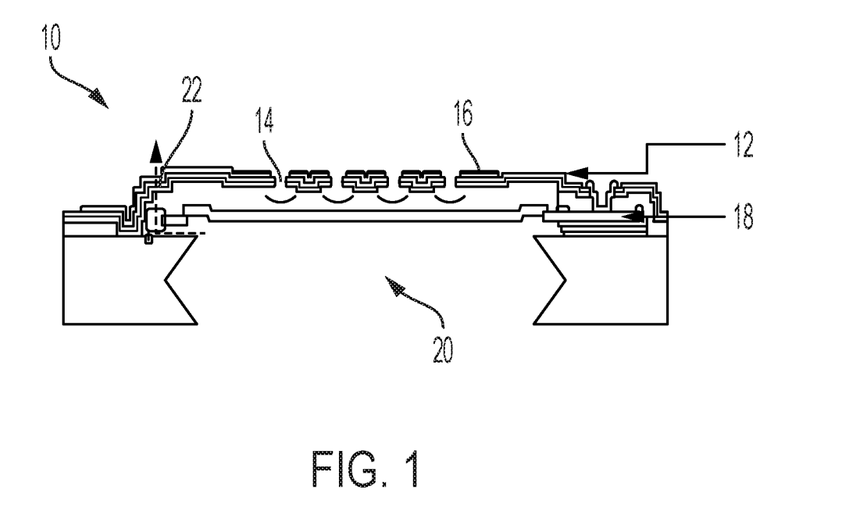
FIG. 1 shows a diagram of a Mircro-ElectroMechanical Systems-(MEMS) microphone.

An example of a MEMS microphone 10 is shown in FIG. 1. The MEMS microphone has a plate 12 that is fixed in place. The plate 12 has holes 14 through which acoustic (mechanical) pressure waves can enter. An electrode 16 permits the MEMS microphone 10 to be operably connected to a system. Located proximate to the fixed plate 12 is a conductive plate 18 that is movable. A chamber 20 is located beneath the conductive plate 18. Compressed air exits through a ventilation hole 22. This MEMs microphone 10 is adapted to measure the vibrations that occur in the environment. However, it should be understood that the MEMS microphone shown in FIG. 1 is by way of example and that other types of MEMS microphones may be used instead. Indeed, it should be understood that any device that is adapted to receive mechanical waves and turn the received mechanical waves into electrical signals can be used so as to take the results of the measured waves and turn it into meaningful information.

A MEMs microphone is able to take mechanical (acoustic) waves that are transmitted through various mediums and convert them into electrical signals. The electrical signals are able to be processed and used to determine information regarding the significance of the mechanical signals that have been measured. Generally, a MEMS microphone is used in order to determine the presence of mechanical waves. In an embodiment, the MEMS microphone is able to measure the mechanical waves and determine the specific frequency of a mechanical wave so measured. In an embodiment, a plurality of MEMS microphones can use the measured mechanical waves and be able to determine position and motion using the measured and processed mechanical waves.

Figure 2:
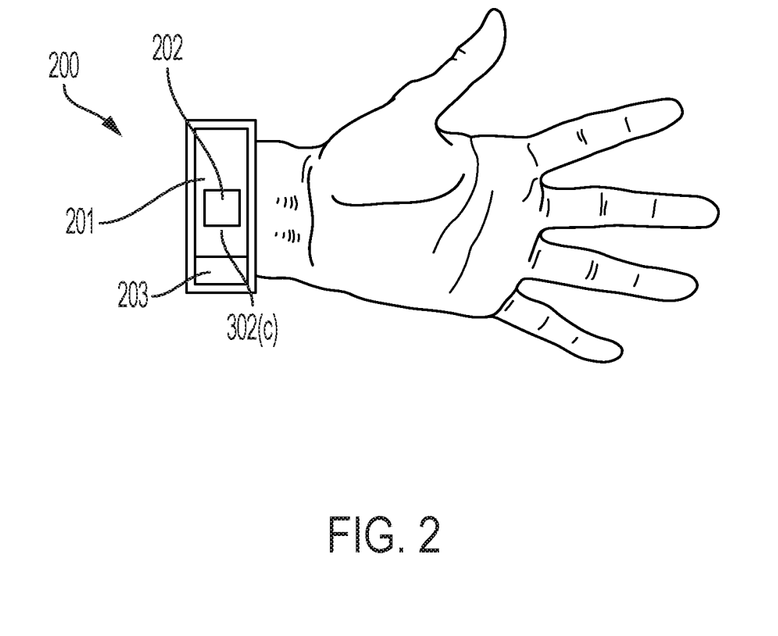
FIG. 2 shows an embodiment of a sensing system incorporating MEMS microphones.

Turning to FIG. 2, sensing system 200 is shown. The sensing system 200 is a mechanical wave measuring system. In the sensing system 200 a MEMS microphone 202 is adapted to be placed on an individual's body. The MEMS microphone 202 is operably attached to or connected to a substrate 201. In an embodiment, the MEMS microphone 202 is formed as part of the substrate 201.

The substrate 201 may form part of a wearable that is worn by a user. The MEMs microphone 202 is able to measure mechanical waves transmitted through the air. Additionally, the MEMs microphone 202 is able to measure mechanical waves transmitted via the user's body. For example, the MEMs microphone 202 is able to detect the presence of mechanical waves transmitted via the dermal layer of a user. In an embodiment, the MEMs microphone measures mechanical waves transmitted through the dermal layer of a user. In an embodiment, the MEMs microphone measures mechanical waves transmitted through the user's body. In an embodiment, the MEMs microphone measures mechanical waves transmitted through the air. In an embodiment, the MEMs microphone measures mechanical waves transmitted through the dermal layer and the interior of a user's body. In an embodiment, the MEMs microphone measures mechanical waves transmitted through the dermal layer, the interior of a user's body and the air.

In an embodiment, the mechanical waves generated by movement of a user's hand are able to be measured by the MEMS microphone. In an embodiment, mechanical waves generated by contact of a user's fingers with another of the user's fingers are measured by the MEMS microphone. In an embodiment, mechanical waves generated by contact of the fingers with parts of the hand are measured by the MEMS microphone. In an embodiment, mechanical waves generated by contact of the fingers with objects are measured by the MEMS microphone. In an embodiment, mechanical waves generated by contact of parts of the hand with other parts of the hand are measured by the MEMS microphone. In an embodiment, mechanical waves generated by contact of objects with parts of the hand are measured by the MEMs microphone. In an embodiment, mechanical waves generated by contact of one hand with another hand is measured by the MEMs microphone. In an embodiment, mechanical waves generated by contact of parts of a body with other body parts or other objects are measured by the MEMS microphone.

The MEMS microphone 202 is operably connected to a processor 203. The processor 203 may be adapted to process and be connected to a plurality of different sensing modalities that are able to measure and determine different facets of motion and position. In an embodiment, the MEMS microphone functions with more than one sensing modality, such as, for example, using transmitting antennas and receiving antennas that transmit and receive a plurality of frequency orthogonal signals and use the received signals to further provide position and movement of a user's hand.

Figure 3:
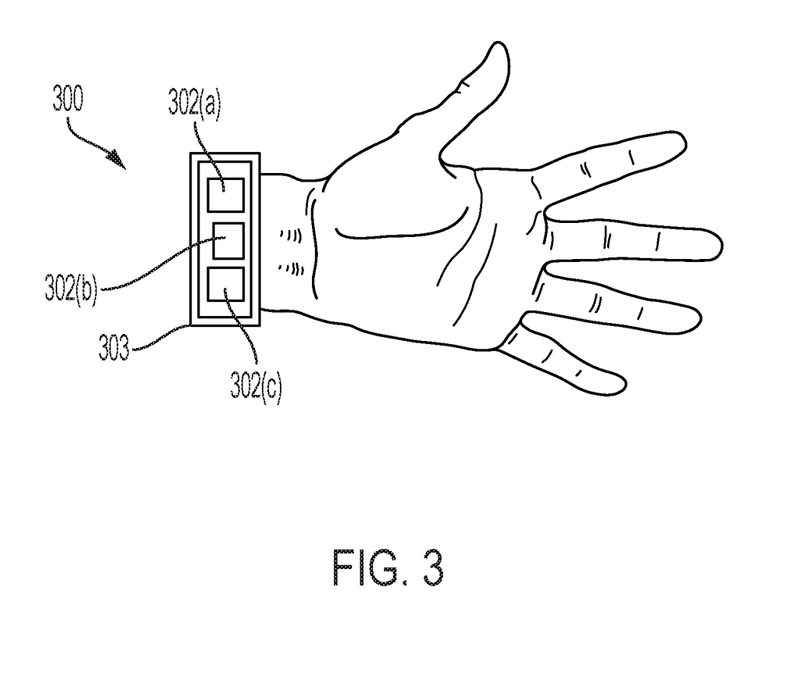
FIG. 3 shows an embodiment of a sensing system having an array of MEMS microphones.

Turning to FIG. 3, sensing system 300 is shown. The sensing system 300 has a MEMS microphone 302(a). The MEMS microphone 302(a) is one MEMS microphone out of a plurality of MEMS microphones. In FIG. 3, three MEMS microphones 302(a)-302(c) are shown. Each one of the MEMs microphones 302(a)-302(c) can be adapted to measure a mechanical wave coming from the activity of a user's hand or body part. The mechanical waves coming from the various activities of a user can be measured with respect to each of the MEMS microphones 302(a)-302(c). The measurements made by each of the MEMS microphones 302(a)-302(c) can be combined and correlated to provide a more comprehensive picture of the movement and activity of a user's body part. A processor 303 processes the measurements and uses the measurements in order to provide information related to motion and position of a user's hand.

The measurement of the mechanical waves can be used to triangulate position as well as to ascertain various qualities of movement extrapolated from the mechanical waves. Because the mechanical waves of contact between various body parts can be measured, properties of the mechanical waves can be used in order to determine the strength of the activity. For example, the mechanical waves of a clap will have different measured properties than the measured properties of the mechanical waves of snap.

Additionally, machine learning can be applied to the data so as to be able to discriminate different activities based on the measured properties of the mechanical waves received. By applying machine learning to the various positions and activities performed by a user the ability of the system to determine position and activity is able to become more refined.

FIG. 3 shows three MEMS microphones, however additional numbers of MEMS microphones as well as different arrays of many MEMS microphones can be used. In an embodiment, an array of four MEMS microphones are positioned in a quadrilateral formation. In an embodiment, an array of four MEMS microphones are positioned along the circumference of a circle. In an embodiment, an array of five MEMS microphones are positioned in a pentagonal formation. In an embodiment, an array of five MEMS microphones are positioned along the circumference of a circle. In an embodiment, an array of six MEMS microphones are positioned in a hexagonal formation. In an embodiment, an array of six MEMS microphones are positioned along the circumference of a circle. It should be understood that larger numbers of MEMS microphones can be used and arranged in various configurations and are not limited to the embodiments disclosed herein. Furthermore, in some embodiments the MEMS microphones can be used in predetermined arrangements that may not form a particular pattern but may instead be determined based on the device or the wearable upon which it is being implemented. For example, if implemented in a glove, a MEMS microphone may be placed within the finger area of each finger portion of a glove.

When the MEMS microphones are positioned along a circumference of a circle formed or placed in or on a wearable that is used by an individual. In an embodiment, the MEMS microphones are placed on or in a wearable placed in the wrist area. In an embodiment, the MEMS microphones are placed on or in a wearable worn in the ankle area. In an embodiment, the MEMS microphones are placed on or in a wearable worn around the neck. In an embodiment, the MEMS microphones are placed on or in a wearable worn around the chest. In an embodiment, the MEMS microphones are placed on or in a wearable worn around the waist. In an embodiment, the MEMS microphones are placed on or in a wearable worn around an arm.

In an embodiment, the MEMS microphones are placed on or in a wearable worn around the head.

Figure 4:
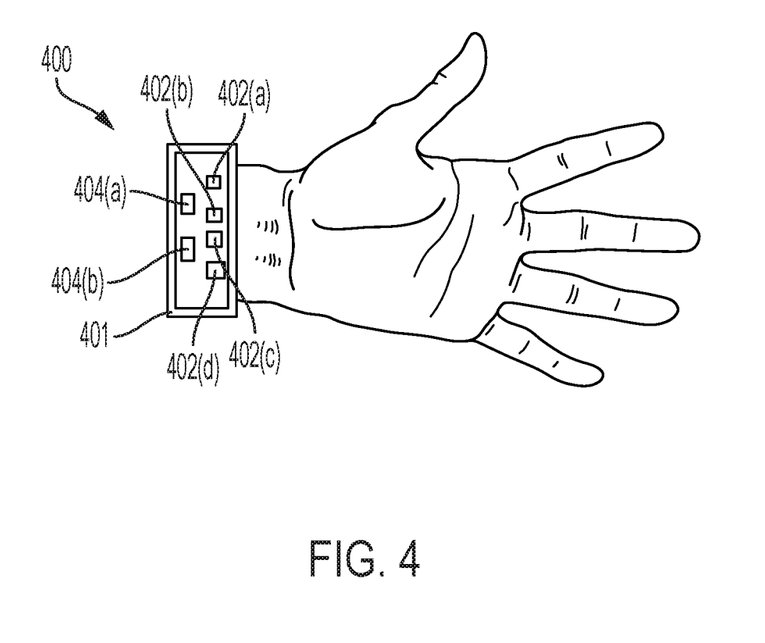
FIG. 4 shows an embodiment of a sensing system having an array of MEMS microphones and mechanical wave transmitters.

Turning to FIG. 4, an embodiment of sensing system 400 is shown. The sensing system 400 has a plurality of MEMS microphones 402(a)-402(d) that are placed on a substrate 401 that is located on a user's body. Additionally, one or more mechanical wave (acoustic) transmitters 404(a)-404(b) can be placed on the substrate 401. The mechanical wave transmitters 404(a)-404(b) are able to generate mechanical waves that can have identifiable frequencies. In an embodiment the mechanical waves are transmitting in a frequency range outside the scope of hearing (generally considered 20 Hz-20 kHz). In an embodiment the mechanical waves are transmitting in a frequency range below 20 Hz. In an embodiment the mechanical waves are transmitting in a frequency range above 20 kHz. In an embodiment the mechanical waves are transmitting in a frequency range below 20 Hz and above 20 kHz. In an embodiment the mechanical waves are transmitting in a frequency range that encompasses part of the hearing range. In an embodiment the mechanical waves are transmitting in a frequency range between 1 Hz-100 kHZ. In an embodiment, the mechanical wave transmitters transmit mechanical waves through air. In an embodiment, the mechanical wave transmitters transmit mechanical waves through the skin. In an embodiment, the mechanical wave transmitters transmit mechanical waves through the interior of the body. In an embodiment, the mechanical wave transmitters transmit mechanical waves through water.

The medium through which the mechanical waves are transmitted will affect the characteristics of the mechanical waves that are transmitted. When the mechanical waves are received by the MEMS microphone and processed, the processor can be adapted to distinguish the particular mechanical wave transmitted by taking into account the medium and accompanying mechanical wave interference. The transmitted mechanical waves can be used to determine movement and position of body parts based on the processed and received mechanical waves.

It should be understood that while the application of mechanical waves (mechanical waves) is discussed via the application of MEMS microphones and mechanical wave emitters, other devices capable of either emitting or receiving mechanical (acoustic) waves can be employed instead of or in addition to the use of the MEMS devices. In an embodiment, the sensing system uses accelerometers. In an embodiment, the sensing system uses accelerometers and MEMS devices. In an embodiment, the sensing system uses piezoelectric devices. In an embodiment, the sensing system uses piezoelectric devices and MEMS devices. In an embodiment, the sensing system uses piezoelectric devices and accelerometers. In an embodiment, the sensing system uses accelerometers, MEMS devices and piezoelectric devices. Sensing systems that employ one or more different types of mechanical wave emitting or receiving devices can further be used with other types of sensing modalities, such as the orthogonal frequency division multiplexing, discussed below.

Figure 5:
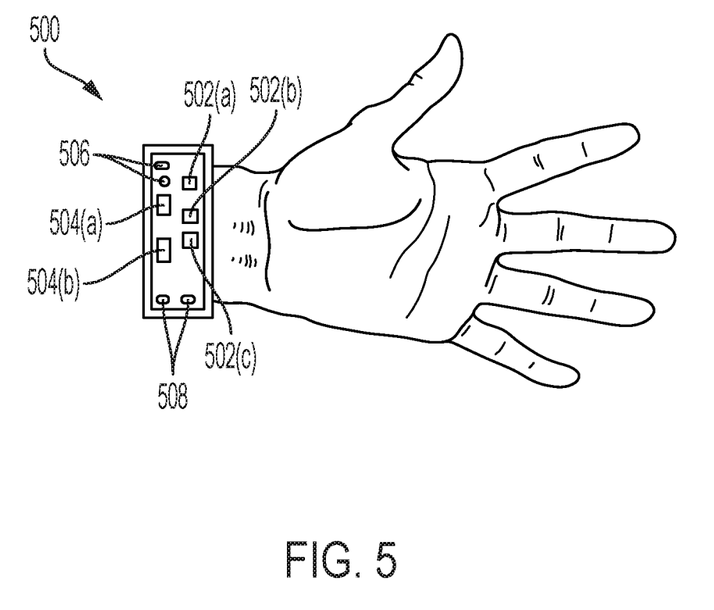
FIG. 5 shows an embodiment of a sensing system having an array of MEMS microphones, transmitting antennas and receiving antennas.

FIG. 5 shows an embodiment of a sensing system 500 that implements MEMS microphones 502(a)-502(c) and mechanical wave transmitters 504(a)-504(b). In addition to the mechanical wave components of the sensing system 500, the sensing system 500 has an additional modality of sensing position and movement of a hand. In particular, the sensing modality implements a plurality of transmitting antennas 506 and a plurality of receiving antennas 508. The plurality of transmitting antennas 506 are adapted to transmit a plurality of unique frequency orthogonal signals that are generated from a signal generator (not shown). When at least one of the plurality of unique frequency orthogonal signals is received, information regarding the position and movement of body parts that interact with the transmitted signals are determined from the measured signals. The received signals may be processed through the use of a Fast Fourier Transform. Further discussion regarding the implementation of the transmitting antennas (or conductors) and receiving antennas (or conductors) can be found in U.S. patent application Ser. No. 15/926,478, U.S. patent application Ser. No. 15/904,953, U.S. patent application Ser. No. 16/383,090 and U.S. patent application Ser. No. 16/383,996, the contents of all of the aforementioned applications incorporated herein by reference.

In the embodiment shown in FIG. 5, the mechanical wave components of the system are able to provide information regarding movement and position of a body part that may not be readily ascertained from other sensing modalities. In particular, the mechanical wave components, such as the MEMS microphones 502(a)-502(c), are able to readily obtain information regarding contact of body parts, such as fingers touching, that may not be easily distinguished from transmitting antennas or receiving antennas.

In an embodiment, the mechanical wave transmitters can each transmit a signal that is frequency orthogonal to each other signal that is transmitted. Certain principles of a fast multi-touch (FMT) sensor have been disclosed in the patent applications disclosed above. With respect to the mechanical wave transmitters, certain principles can be applied to the acoustic signals (mechanical waves) that are transmitted. Orthogonal signals may be transmitted and information may be received by the MEMS microphones. In an embodiment, receivers "sample" the signals received during a sampling period (T). In an embodiment, signals are then analyzed by a signal processor to identify events (including, position and movement of body parts). In an embodiment, one or more transmitters can transmit a signal and the movement of the respective body parts impacts the signals that are received and processed. In an embodiment where the orthogonal signals are frequency orthogonal, spacing between the orthogonal frequencies, Of, may be at least the reciprocal of the measurement period T, the measurement period T being equal to the period during which the column conductors are sampled. Thus, in an embodiment, the received at a column conductor may be measured for one millisecond (T) using frequency spacing ($\Delta f$) of one kilohertz (i.e., $\Delta f=1/\tau$).

In an embodiment, a signal processor of a mixed signal integrated circuit (or a downstream component or software) is adapted to determine at least one value representing each frequency orthogonal signal transmitted. In an embodiment, the signal processor of the mixed signal integrated circuit performs a Fourier transform on the signals received. In an embodiment, the mixed signal integrated circuit is adapted to digitize received signals. In an embodiment, the mixed signal integrated circuit is adapted to digitize the signal and perform a discrete Fourier transform (DFT) on the digitized information. In an embodiment, the mixed signal integrated circuit (or a downstream component or software) is adapted to digitize the signals present on the received conductor or antenna and perform a Fast Fourier transform (FFT) on the digitized information—an FFT being one type of discrete Fourier transform.

It will be apparent to a person of skill in the art in view of this disclosure that a DFT, in essence, treats the sequence of digital samples (e.g., window) taken during a sampling period (e.g., integration period) as though it repeats. As a consequence, signals that are not center frequencies (i.e., not integer multiples of the reciprocal of the integration period (which reciprocal defines the minimum frequency spacing)), may have relatively nominal, but unintended consequence of contributing small values into other DFT bins. Thus, it will also be apparent to a person of skill in the art in view of this disclosure that the term orthogonal as used herein is not "violated" by such small contributions. In other words, as the term frequency orthogonal is used herein, two signals are considered frequency orthogonal if substantially all of the contribution of one signal to the DFT bins is made to different DFT bins than substantially all of the contribution of the other signal.

An example of such a sampled signal is as follows. In an embodiment, received signals are sampled at 4.096 Mhz. In an embodiment, received signals are sampled at more than 4 MHz. To achieve kHz sampling, for example, 4096 samples may be taken at 4.096 MHz. In such an embodiment, the integration period is 1 millisecond, which per the constraint that the frequency spacing should be greater than or equal to the reciprocal of the integration period provides a minimum frequency spacing of 1 KHz. (It will be apparent to one of skill in the art in view of this disclosure that taking 4096 samples at e.g., 4 MHz would yield an integration period slightly longer than a millisecond, and not achieving kHz sampling, and a minimum frequency spacing of 976.5625 Hz.) In an embodiment, the frequency spacing is equal to the reciprocal of the integration period. In such an embodiment, the maximum frequency of a frequency-orthogonal signal range should be less than 2 MHz. In such an embodiment, the practical maximum frequency of a frequency-orthogonal signal range should be less than about 40% of the sampling rate, or about 1.6 MHz. In an embodiment, a DFT (which could be an FFT) is used to transform the digitized received signals into bins of information, each reflecting the frequency of a frequency-orthogonal signal transmitted which may have been transmitted by the transmitting antenna. In an embodiment 2048 bins correspond to frequencies from 1 KHz to about 2 MHz. It will be apparent to a person of skill in the art in view of this disclosure that these examples are simply that, exemplary. Depending on the needs of a system, and subject to the constraints described above, the sample rate may be increased or decreased, the integration period may be adjusted, the frequency range may be adjusted, etc.

In an embodiment, a DFT (which can be an FFT) output comprises a bin for each frequency-orthogonal signal that is transmitted. In an embodiment, each DFT (which can be an FFT) bin comprises an in-phase (I) and quadrature (Q) component. In an embodiment, the sum of the squares of the I and Q components is used as a measure corresponding to signal strength for that bin. In an embodiment, the square root of the sum of the squares of the I and Q components is used as measure corresponding to signal strength for that bin. It will be apparent to a person of skill in the art in view of this disclosure that a measure corresponding to the signal strength for a bin could be used as a measure related to muscle activity. In other words, the measure corresponding to signal strength in a given bin would change as a result of some activity originated by muscles of the body.

An aspect of the present disclosure is a mechanical wave sensing system. The mechanical wave sensing system comprises a substrate adapted to be located on a user's body; a plurality of MEMS microphones adapted to receive mechanical waves, wherein at least one of the plurality of MEMS microphones is operably attached to the substrate; a processor operably connected to the plurality of MEMS microphones and the plurality of receiving antennas, wherein the processor is adapted to process measurements of the mechanical waves received by the plurality of MEMS microphone and to determine information regarding movement of a body part using the measurements.

Another aspect of the present disclosure is a system. The system comprises a substrate; a plurality of MEMS microphones adapted to receive mechanical waves, wherein at least one of the plurality of MEMS microphones is operably attached to the substrate; a plurality of transmitting antennas, wherein at least one of the plurality of transmitting antennas is operably connected to a signal generator wherein the signal generator is adapted to generate a plurality of unique frequency orthogonal signals and each of the plurality of unique frequency orthogonal signals frequency orthogonal to each other; a plurality of receiving antennas, wherein the plurality of receiving antennas are adapted to receive the plurality of unique frequency orthogonal signals; and a processor operably connected to the plurality of MEMS microphones and the plurality of receiving antennas, wherein the processor is adapted to process measurements of the mechanical waves received by the plurality of MEMS microphone and to process measurements of received unique frequency orthogonal signals, wherein processed measurements of the mechanical waves and received unique frequency orthogonal signals are used to determine information regarding movement of a body part.

Still yet another aspect of the disclosure is a mechanical sensing system. The mechanical wave sensing system comprises a substrate; a MEMS microphone operably connected to the substrate and adapted to receive mechanical waves; an mechanical wave transmitter operably attached to the substrate; and a processor operably connected to the MEMS microphone, wherein the processor is adapted to process measurements of the mechanical waves received by the MEMS microphone and determine information regarding movement of a hand.

While the invention has been particularly shown and described with reference to a preferred embodiment thereof, it will be understood by those skilled in the art that various changes in form and details may be made therein without departing from the spirit and scope of the invention.

The invention claimed is:

1. A mechanical wave sensing system, comprising:
   a substrate adapted to be located on a user's body;
   a plurality of micro-electromechanical system (MEMS) microphones adapted to receive mechanical waves, wherein at least one of the plurality of MEMS microphones is operably attached to the substrate;
   a processor operably connected to the plurality of MEMS microphones, wherein the processor is adapted to process measurements of the mechanical waves received by the plurality of MEMS microphone using a discrete Fourier transform to determine information regarding movement of a body part using the measurements; and
   a mechanical wave transmitter operably attached to the substrate, wherein the mechanical wave transmitter is adapted to transmit mechanical waves at a predetermined frequency towards the user's body, wherein the mechanical wave transmitter transmits mechanical waves at a frequency higher than 20 kHz, wherein the mechanical wave transmitter is one of a plurality of mechanical wave transmitters and each of the plurality of mechanical wave transmitters transmits at a unique frequency.

2. The mechanical wave sensing system of claim 1, wherein the plurality of MEMS microphones are arranged along a perimeter of a wrist of the user.

3. The mechanical wave sensing system of claim 1, wherein the substrate is adapted to be worn on a wrist.

4. The mechanical wave sensing system of claim 1, wherein the mechanical wave transmitter is adapted to transmit waves into a dermal layer of the user of the mechanical sensing system.

5. The mechanical wave sensing system of claim 1, wherein the determined information regarding movement is contact between fingers of a hand.

6. A mechanical wave sensing system, comprising:
a substrate;
a micro-electromechanical system (MEMS) microphone operably connected to the substrate and adapted to receive mechanical waves;
a mechanical wave transmitter operably attached to the substrate, wherein the mechanical wave transmitter is adapted to transmit mechanical waves at a predetermined frequency towards a hand, wherein the mechanical wave transmitter is one of a plurality of mechanical wave transmitters and each of the plurality of mechanical wave transmitters transmits at a unique frequency, wherein the mechanical wave transmitter transmits mechanical waves at a frequency higher than 20 kHz; and
a processor operably connected to the MEMS microphone, wherein the processor is adapted to process measurements of the mechanical waves received by the MEMS microphone using a discrete Fourier transform and determine information regarding movement of the hand.

* * * * *